United States Patent
Franz et al.

(10) Patent No.: US 10,031,041 B2
(45) Date of Patent: Jul. 24, 2018

(54) ROPE LEAK SENSOR HOLDER

(71) Applicant: Hewlett Packard Enterprise Development LP, Houston, TX (US)

(72) Inventors: John Franz, Houston, TX (US); Phi A Nguyen, Houston, TX (US)

(73) Assignee: HEWLETT PACKARD ENTERPRISE DEVELOPMENT LP, Houston, TX (US)

( * ) Notice: Subject to any disclaimer, the term of this patent is extended or adjusted under 35 U.S.C. 154(b) by 232 days.

(21) Appl. No.: 15/185,872

(22) Filed: Jun. 17, 2016

(65) Prior Publication Data

US 2017/0363501 A1 Dec. 21, 2017

(51) Int. Cl.
*G01M 3/16* (2006.01)
*G01N 27/04* (2006.01)
*G01N 27/22* (2006.01)
*G01R 27/26* (2006.01)

(52) U.S. Cl.
CPC .......... *G01M 3/16* (2013.01); *G01N 27/048* (2013.01); *G01R 27/2605* (2013.01)

(58) Field of Classification Search
CPC .......... G01M 3/00; G01M 3/02; G01M 3/04; G01M 3/16; G01N 27/00; G01N 27/02; G01N 27/04; G01N 27/048; G01R 27/00; G01R 27/02; G01R 27/26; G01R 27/2605; G01D 5/00; G01D 5/12; G01D 5/14; G01D 5/24; G01D 5/2405

USPC ....... 324/600, 649, 658, 663, 664, 686, 689, 324/691, 693, 694; 269/20, 21, 23, 30, 269/35, 287, 288, 291, 296, 302, 303, 269/305
See application file for complete search history.

(56) References Cited

U.S. PATENT DOCUMENTS

| | | | |
|---|---|---|---|
| 2,743,743 A | | 5/1956 | Galloup |
| 4,663,963 A | * | 5/1987 | Veyrat ...................... B07C 5/34 73/45 |
| 4,672,366 A | * | 6/1987 | Butts .................... B65D 90/503 340/605 |
| 4,920,786 A | * | 5/1990 | Danielson ............ B65D 90/501 220/560.03 |
| 8,786,452 B1 | | 7/2014 | Kreitz et al. |
| 2002/0088931 A1 | | 7/2002 | Danisch et al. |
| 2008/0053198 A1 | * | 3/2008 | Issel ........................ F16L 11/12 73/40.5 R |
| 2011/0120576 A1 | * | 5/2011 | Sigouin ................... G01M 3/04 137/551 |
| 2013/0292319 A1 | * | 11/2013 | Fulkerson ........... A61M 1/1692 210/321.78 |

FOREIGN PATENT DOCUMENTS

| CN | 203773701 U | 8/2014 |
|---|---|---|
| CN | 204990640 U | 1/2016 |

* cited by examiner

*Primary Examiner* — Hoai-An D Nguyen
(74) *Attorney, Agent, or Firm* — Hewlett Packard Enterprise Patent Department (57) ABSTRACT

Example implementations relate to a rope leak sensor holder segment. For example, in an implementation, a rope leak sensor holder segment includes an elongated track and a channel to accept a rope leak sensor. The rope leak sensor holder segment includes a retainer to secure the rope leak sensor within the channel.

15 Claims, 10 Drawing Sheets

FIG. 12

ROPE LEAK SENSOR HOLDER

BACKGROUND

A rope leak sensor may include two physically parallel conduction paths. Fluid in contact with the rope leak sensor may conduct electricity across the parallel conduction paths. Presence of the fluid may be detected by monitoring impedance along the rope leak sensor.

BRIEF DESCRIPTION OF THE DRAWINGS

Various examples will be described below with reference to the following figures.

Throughout the drawings, identical reference numbers may designate similar, but not necessarily identical, elements. Additionally, use herein of a reference numeral without a hyphenated index number, where such reference numeral is referred to elsewhere with a hyphenated index number, may be a general reference to the corresponding plural elements, collectively or individually.

DETAILED DESCRIPTION

Some computing systems, such as high performance computing systems, may be liquid cooled. Such systems may employ leak detection devices to monitor for leaks of the liquid cooling. Examples of leak detection devices may include rope-style leak sensors comprising physically parallel and/or intertwined conduction paths or wires. The parallel or intertwined conduction paths may be electrically connected in series by a known impedance (e.g., a fixed resistance) at a terminal end of the rope leak sensor. The rope leak sensor may be placed in a drain pan under the computing system, and coolant in the drain pan may result in a detectable short circuit between the conduction paths when monitoring the impedance along the rope leak sensor.

In some cases, the rope leak sensor is laid bare in the drain pan, and in other cases, the rope leak sensor may be clipped to the drain pan. In either case, the rope leak sensor may kink or buckle and thus not lie flat in the drain pan. Additionally, some installations elevate the rope leak sensor above the drain pan floor. However, in order to detect leaks early and accurately and to thus enable quick leak mitigation, the rope leak sensor should remain flat against the bottom of the drain pan. Additionally, failed or defective sensors may need to be removed and replaced, but the size of some computing systems may reduce access to the rope leak sensor in the drain pan and to securing mechanisms such as clips.

Examples disclosed herein may relate to, among other things, a rope leak sensor holder segment. In some implementations, the rope leak sensor holder segment includes an elongated track and a channel running lengthwise in the elongated track to accept a rope leak sensor. The rope leak sensor holder segment may include retaining tabs to secure the rope leak sensor within the channel. In some implementations, the channel is in an underside of the track and an open region of the channel faces downward. By virtue of assembling a rope leak sensor to an example rope leak sensor holder segment as described herein, the rope leak sensor may be placed flat against the drain pan to improve speed and consistency of leak detection.

Figure 1:
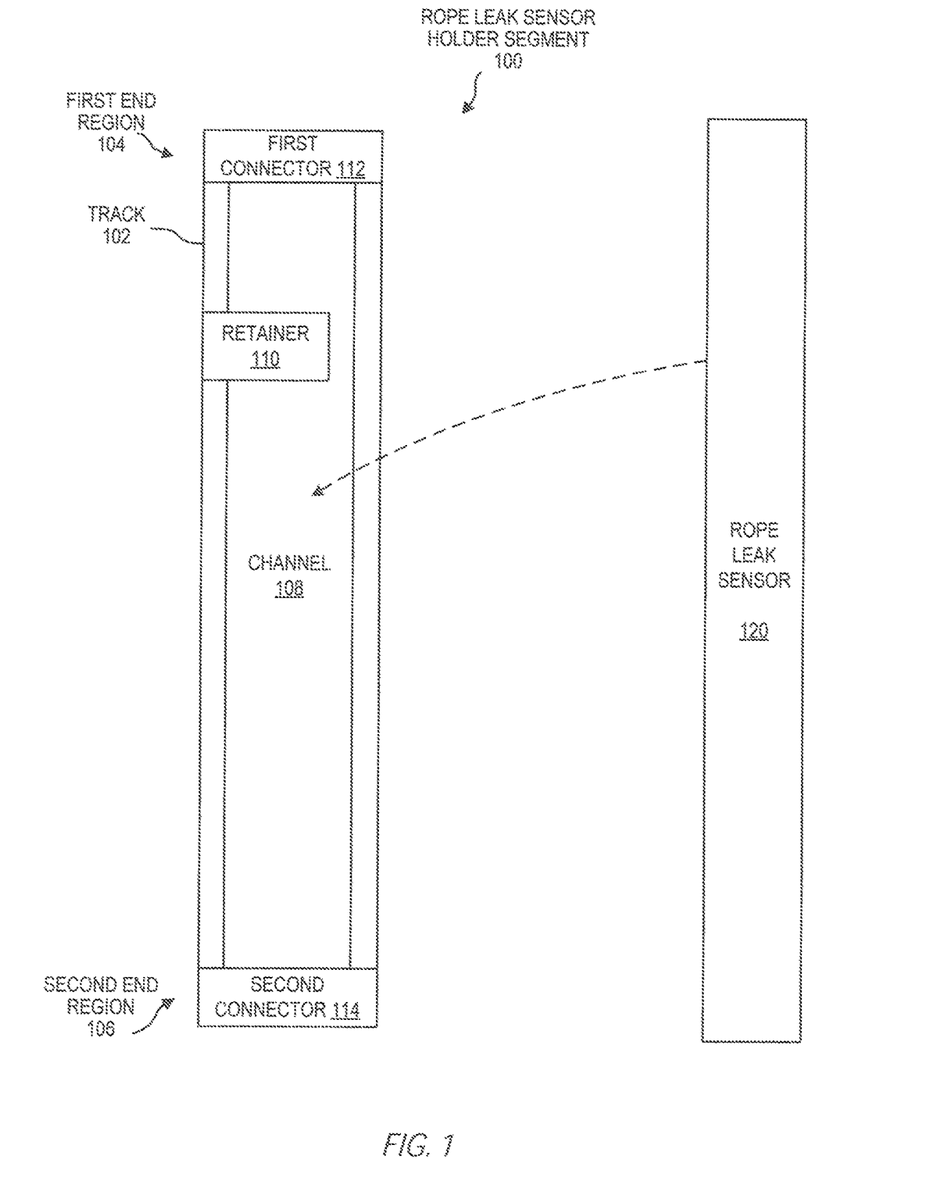
FIG. 1 is a block diagram of an example rope leak sensor holder segment.

Referring now to the figures, FIG. 1 depicts a block diagram of an example rope leak sensor holder segment 100. The rope leak sensor holder segment 100 includes an elongated track 102 having a first end region 104 and a second end region 106. In other words, the track 102 has a long axis running from the first end region 104 to the second end region 106 (also referred to as a lengthwise direction or along the length of the track 102). A width and height of the track 102 may be orthogonal to that long axis. In some cases, the track 102 may be understood to form a main body of the rope leak sensor holder segment 100. Rope leak sensor holder segments described herein may also be referred to as holder segments for convenience.

The holder segment 100 also includes a channel 108 in the track 102 extending from the first end region 104 to the second end region 106. The channel 108 is to accept a rope leak sensor 120, as illustrated in FIG. 1 by the dashed arrow. The channel 108 may extend through the first end region 104 and the second end region 106, such that the ends of the holder segment 100 are open and the rope leak sensor 120 may extend beyond the holder segment 100 when assembled to the holder segment 100.

The holder segment 100 also may include a retainer 110 to secure the rope leak sensor within the channel 108. Various implementations of the retainer 110 will be described below. In some cases, the retainer 110 (and together with other aspects of the holder segment 100) may maintain the rope leak sensor 120 substantially straight and flat, and minimize kinking, bending, sagging, or other deformations of the rope leak sensor 120.

The holder segment 100 also may include a first connector 112 at the first end region 104 and a second connector 114 at the second end region 106. The second connector 114 may be complementary to the first connector 112, so that multiple holder segments 100 may be joined together by joining the first connector (112) of a first holder segment to the second connector (114) of an adjacent second holder segment. For example, the first connector 112 and the second connector 114 may be complementary in that they are corresponding parts of a latch closure, are sized or toleranced for an interference fit, are corresponding parts of a hook-and-loop system, are magnetic, etc.

Figure 2:
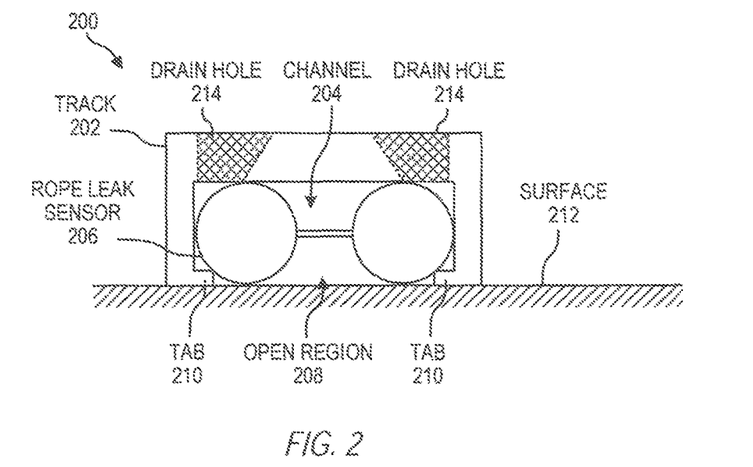
FIG. 2 depicts an example rope leak sensor holder segment with tab retainers.

FIG. 2 depicts an example rope leak sensor holder segment 200 with tab retainers. More particularly, FIG. 2 shows an end-on or cross-sectional view of a rope leak sensor holder segment 200 (i.e., a view plane orthogonal to the long axis described above). The holder segment 200 may include a track 202 with a channel 204, which may be analogous in many respects to the track 102 and the channel 108, respectively. A rope leak sensor 206 may be assembled into the channel 204. In some implementations, the channel 204 may include an open region 208 (i.e., an open face) by which the rope leak sensor 206 may be exposed to the environment. The size of the channel 204, particularly the width and height visible in FIG. 2, may be selected to accommodate the rope leak sensor 206 to be used with the holder segment 200.

The holder segment 200 may include a plurality of tabs 210 that protrude from the track 202 and extend at least partially over the open region 208 of the channel 204, thus securing the rope leak sensor 206 to the channel 204. In some implementations, the tabs 210 may be distributed along the length of the track 202. The tabs 210 may serve as or form part of the retainer 110 described above.

The channel 204 may be in an underside of the track 202, and the open region 208 of the channel 204 may face downward. Thus, when the holder segment 200 is placed on a surface 212, such as a drain pan, the rope leak sensor 206 may be placed low and close to the surface 212 or even in contact with the surface 212. Owing to placement close to or on the surface 212, the rope leak sensor 206 may be exposed early to any fluid on the surface 212.

The holder segment 200 also may include at least one drain hole 214 through the track 202, extending from an outer surface of the track 202 to the channel 204. In some implementations, the track 202 may include sloped collection surfaces that funnel fluid towards drain holes 214 or such sloped surfaces may form part of the drain holes 214 themselves. The drain holes 214 may allow fluid to come into contact with the rope leak sensor 206, rather than the fluid being shielded off by the track 202 above the rope leak sensor 206.

Figure 3:
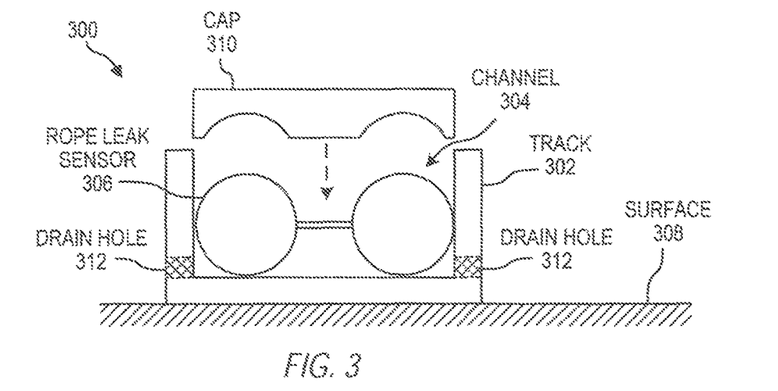
FIG. 3 depicts an example rope leak sensor holder segment with a cap retainer.

FIG. 3 depicts an example rope leak sensor holder segment 300 with a cap retainer. The holder segment 300 may include a track 302 and a channel 304 within the track 302. The track 302 and the channel 304 may be analogous in many respects to the track 102 and the channel 108, respectively. In some implementations, the holder segment 300 may be oriented such that the channel 304 is open upward. A rope leak sensor 306 may be assembled into the channel 304. The holder segment 300 may be placed on a surface 308, such as a drain pan.

The holder segment 300 may include a cap 310 that fits into the channel 304. In some implementations, the cap may be removable. With a rope leak sensor 306 placed in the channel 304, the cap 310 may be pressed into the channel 304 to secure the rope leak sensor 306 in the channel 304. The cap 310 may serve as or form part of the retainer 110 described above. In some implementations, the cap 310 may include a plurality of caps 310 pressed into the channel 304 at various points along the length of the holder segment 300, thus leaving some portions of the rope leak sensor 306 exposed to fluid entering the channel 304 from above. In some implementations, the cap 310 may extend along at least a portion of the length of the holder segment 300.

In some implementations, the holder segment 300 may include at least one drain hole 312 extending through the track 302 and into the channel 304, and more particularly, through a sidewall of the track 302. By virtue of the drain hole(s) 312, fluid on the surface 308 may flow into the channel 304 and be detected by the rope leak sensor 306.

Figure 4:
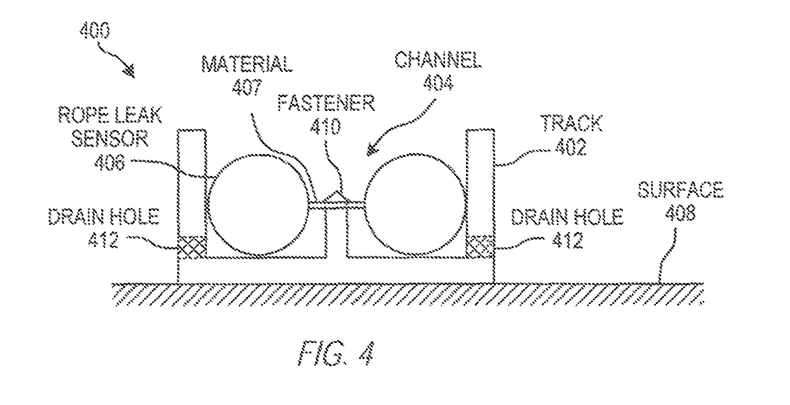
FIG. 4 depicts an example rope leak sensor holder segment with a fastener-type retainer.

FIG. 4 depicts an example rope leak sensor holder segment 400 with a fastener for a retainer. The holder segment 400 may include a track 402 and a channel 404 within the track 402. The track 402 and the channel 404 may be analogous in many respects to the track 102 and the channel 108, respectively. In some implementations, the holder segment 400 may be oriented such that the channel 404 is open upward. The holder segment 400 may be placed on a surface 408, such as a drain pan.

A rope leak sensor 406 may be assembled into the channel 404. For example, the rope leak sensor 406 may feature two parallel cloth-covered wires connected by a material 407, such as a mesh or fabric.

The holder segment 400 may include a fastener 410, such as a rivet, a staple, a pin, a bolt, a screw, a tack, etc., to hold on to the material 407 of the rope leak sensor 406 and thereby retain the rope leak sensor 406 within the channel 404. In some implementations, the fastener 410 may be part of the track 402. In some implementations, the fastener 410 may be separately attached or assembled to the track 402.

In a manner similar to the holder segment 300, the holder segment 400 may, in some implementations, include at least one drain hole 412 extending through the track 402 and into the channel 404, and more particularly, through a sidewall of the track 402. By virtue of the drain hole 412, fluid on the surface 408 may flow into the channel 404 and be detected by the rope leak sensor 406. Additionally, the rope leak sensor 406 may remain exposed to fluid entering the channel 404 from above.

Figure 5:
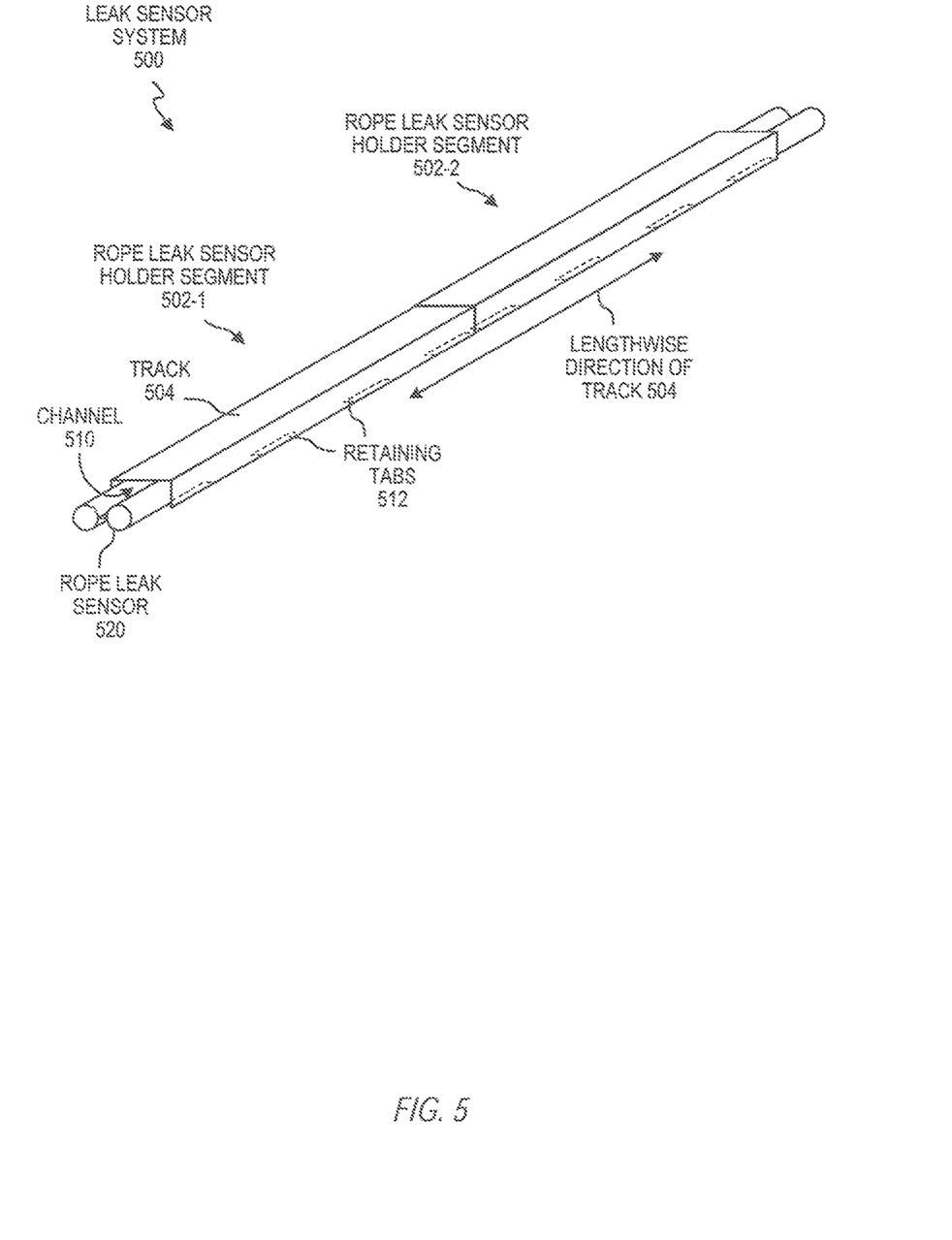
FIG. 5 depicts an example leak sensor system.

FIG. 5 depicts an example leak sensor system 500. The leak sensor system 500 includes a rope leak sensor 520 and a plurality of rope leak sensor holder segments 502 (e.g., 502-1 and 502-2, although additional segments not depicted may be included). Each rope leak sensor holder segment 502 may include an elongated track 504. In some implementations, each holder segment 502 may be substantially similar in length (e.g., within a manufacturing tolerance, etc.) or may be of different lengths, depending on the application. Each holder segment 502 may include a channel 510 running lengthwise in the track 504.

In some implementations, a holder segment 502 may include retaining tabs 512 along the track 504 that extend at least partially across an open region of the channel 510. For example, tabs 512 may be analogous in many respects to the tabs 210 described above. In this manner, the holder segments 502 as depicted may be similar in many respects to the holder segment 200 described above, although other holder segments, such as holder segments 100, 300, 400, may be employed as holder segments in the leak sensor system 500. The rope leak sensor 520 may be assembled into the channel 510 of each rope leak sensor holder segment 502 and retained or held in place by the retaining tabs 512.

In some implementations, the plurality of rope leak sensor holder segments 502 may be oriented to face the open region of the channel 510 downward, as is depicted in FIG. 5. Accordingly, in FIG. 5, the tabs 512 are on an underside of the track 504, and are thus depicted as hidden surfaces in broken lines.

Figure 6:
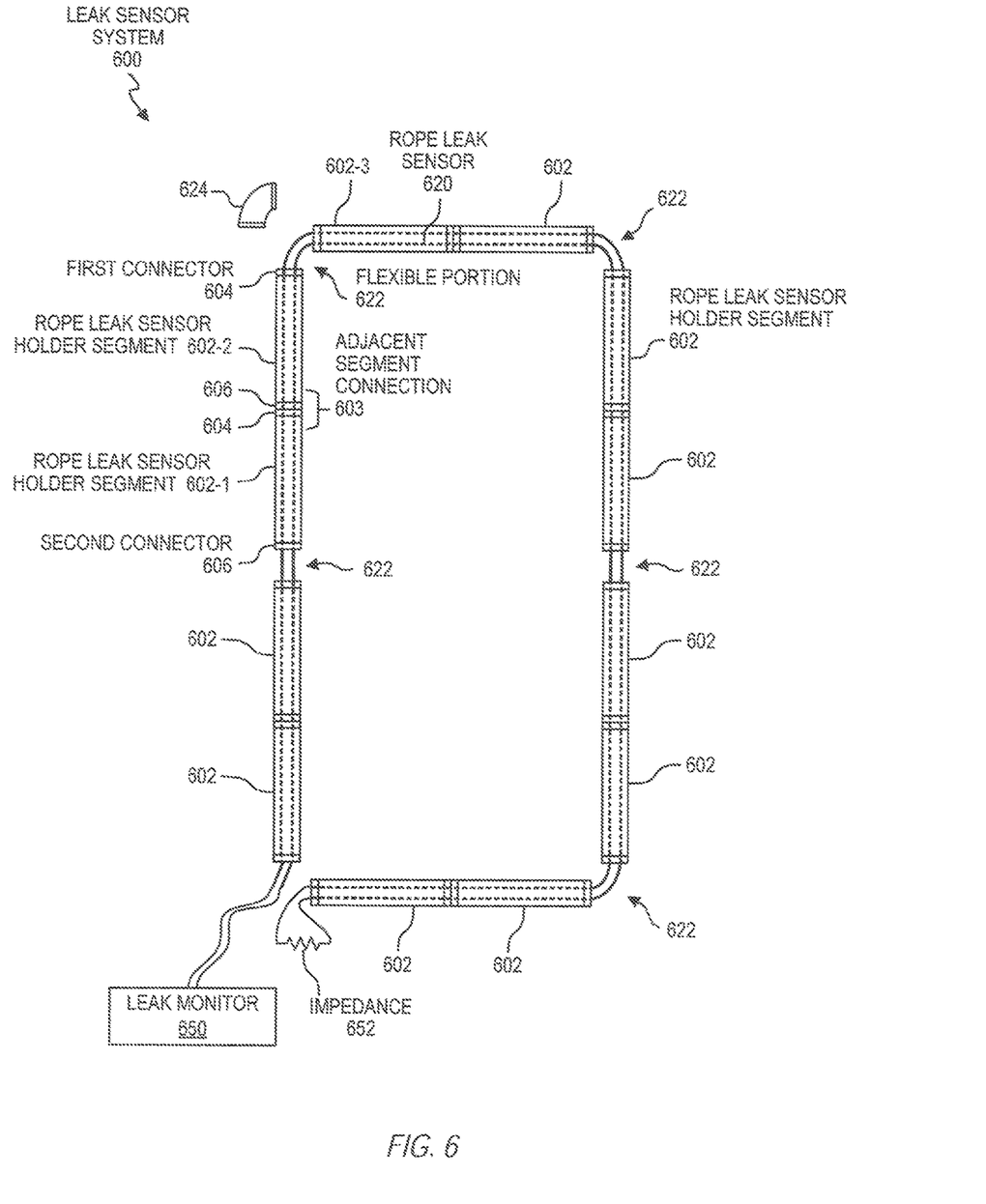
FIG. 6 depicts another example leak sensor system.

FIG. 6 depicts another example leak sensor system 600. The leak sensor system 600 may include a plurality of rope leak sensor holder segments 602. FIG. 6 references some holder segments 602 specifically for the purposes of illustration, namely holder segments 602-1, 602-2, 602-3.

Each holder segment 602 may be formed as an elongated track with a channel running lengthwise in the track, in a manner similar to the holder segment 100 or 502 as described above for example. A rope leak sensor 620 may be assembled into the channels of the holder segments 602 (portions of rope leak sensor 620 in the holder segments 602 are depicted as dashed line segments), and may be retained in the channels by a retainer, such as those described above with respect to FIGS. 2, 3, 4 or other retainers. In some implementations, the holder segments 602 include drain holes that extend through the track from into the channel. For example, where the holder segment 602 is configured analogously to the holder segment 200 described above, drain holes extend from an upper surface of the track into the channel below.

In some implementations, the rope leak sensor 620 may include two physically parallel conductors (e.g., wires) joined at one end by an impedance 652 (e.g., a resistor) and connected at the other end to a leak monitor 650. When no leak is detected, the leak monitor 650 reads an impedance along the rope leak sensor 620 that is a function of the impedance 652. When a leak occurs, a short circuit is established between the physically parallel conductors where leaked fluid comes into contact with the rope leak sensor 620, and the leak monitor 650 reads a different impedance indicating the presence of fluid.

Each holder segment 602 also may include a first connector 604 at a first end region of the track and a second connector 606 at a second end region of the track. In some implementations, the first connector 604 and the second connector 606 may be analogous in many respects to the first connector 112 and the second connector 114 of holder segment 100 described above. The first connector 604 and the second connector 606 may be complementary parts of a connection system. Separate rope leak sensor holder segments 602 may be joined by mating the first connector and the second connector of respective adjacent rope leak sensor holder segments. For example, a first connector 604 of the holder segment 602-1 may be joined to a second connector 606 of the holder segment 602-2 to form a connection 603 between adjacent segments 602-1 and 602-2.

In some implementations, the leak sensor system 600 may include a flexible portion 622, which is a portion of the rope leak sensor 620 between adjacent and unconnected rope leak sensor holder segments. In other words, the flexible portion 622 may be a portion of the rope leak sensor 620 that is not assembled into a sensor holder 602. As but one example, FIG. 6 depicts a flexible portion 622 bent into a corner between adjacent but unconnected holder segments 602-2 and 602-3.

In some implementations, a corner finishing element may be provided to set an angle of the flexible portion. As but one example, FIG. 6 depicts a ninety-degree (90°) corner finishing element 624, which may be similar to the holder segments 602 (i.e., including a track with a channel therein) but curved. In other implementations, the corner finishing element may be a hinge, a spring, a guide rod, or other rigid or semi-rigid structure.

By assembling some portions of the rope leak sensor 620 to holder segments 602 and maintaining other portions of the rope leak sensor 620 as flexible portions 622, ease of handling of the rope leak sensor 620 (and more generally, the leak sensor system 600) may be improved, particularly for installation in and removal from a drain pan for example. Rigidity provided by the holder segments 602 facilitates pushing the leak sensor system 600, while flexibility at the flexible portions 622 facilitates maneuvering and positioning the leak sensor system 600 around corners. Moreover, the holder segments 602 may aid in situating the rope leak sensor 620 as flat and as low as possible in the drain pan, thus facilitating early detection of fluid leaks. Furthermore, owing to the flexible portions 622, the leak sensor system 600 may be folded into a compact package for storage or shipping. By virtue of the foregoing, the leak sensor system 600 may be a field replaceable unit.

Figure 7:
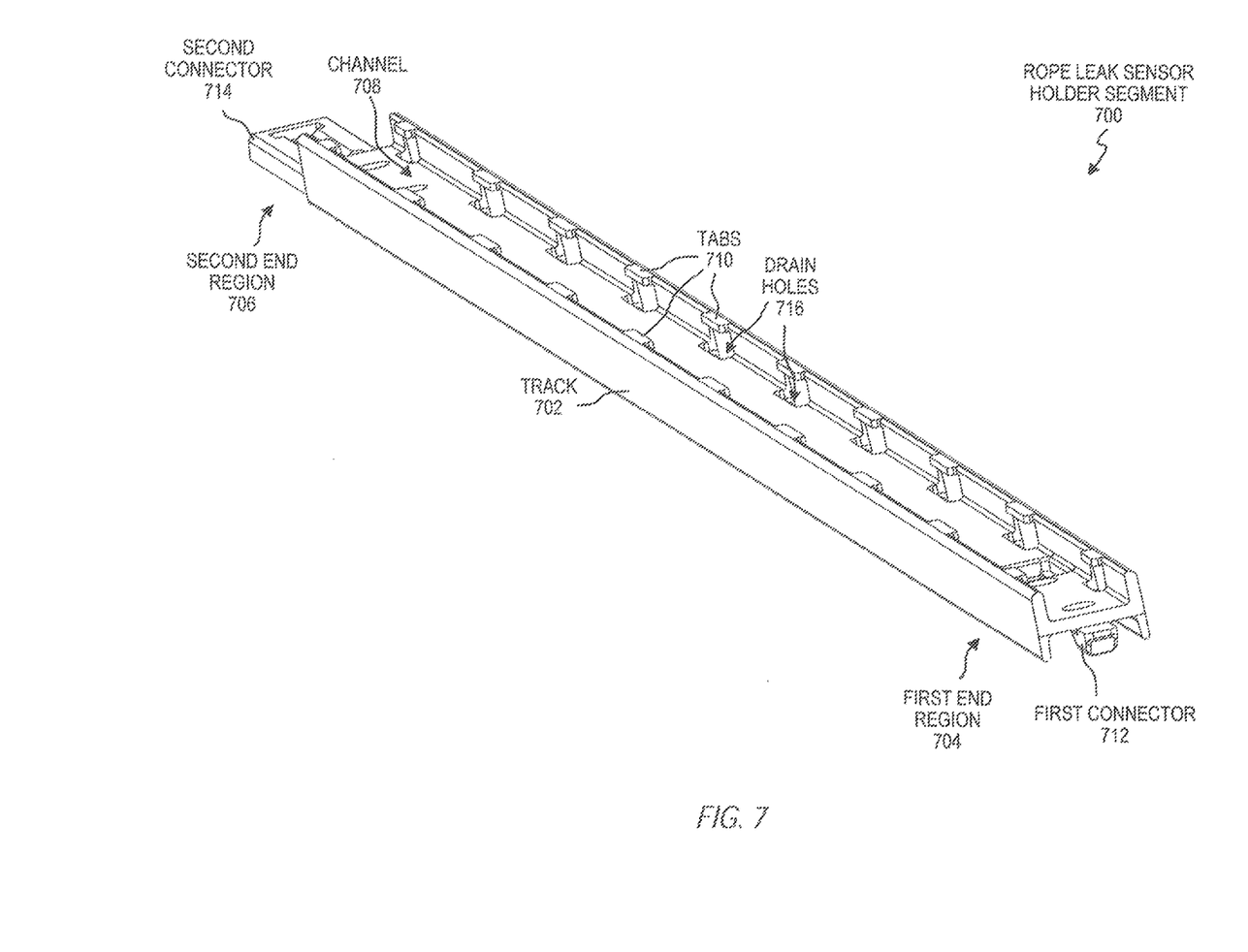
FIG. 7 depicts an example rope leak sensor holder segment, with a channel being visible.

FIG. 7 depicts an example rope leak sensor holder segment 700 that includes a track 702 with a first end region 704 and a second end region 706. A channel 708 runs lengthwise in the track 702 from the first end region 704 to the second end region 706. The holder segment 700 includes tabs 710 to secure a rope leak sensor within the channel 708. The holder segment 700 also includes a first connector 712 at the first end region 704 and a second connector 714 at the second end region 706. The first connector 712 and the second connector 714 may be complementary, so as to enable multiple holder segments 700 to be joined.

The holder segment 700 includes drain holes 716 by which fluid may enter the channel 708 from a side or surface of the track 702 opposite the channel 708 (not visible in FIG. 7). In the example depicted in FIG. 7, the drain holes 716 are aligned with the tabs 710, although other arrangements may be employed, such as the tabs 710 and drain holes 716 being offset from one another.

The holder segment 700 may be an example implementation of the holder segments 100, 200, 502, or 602. In some implementations, the view shown in FIG. 7 is a perspective view that includes a view of the bottom of the holder segment 700. In other words, in operation, the holder segment 700 may be placed on a surface (e.g., a drain pan) with the opening of the channel 708 facing downwards and the tabs in contact with the surface.

Figure 8:
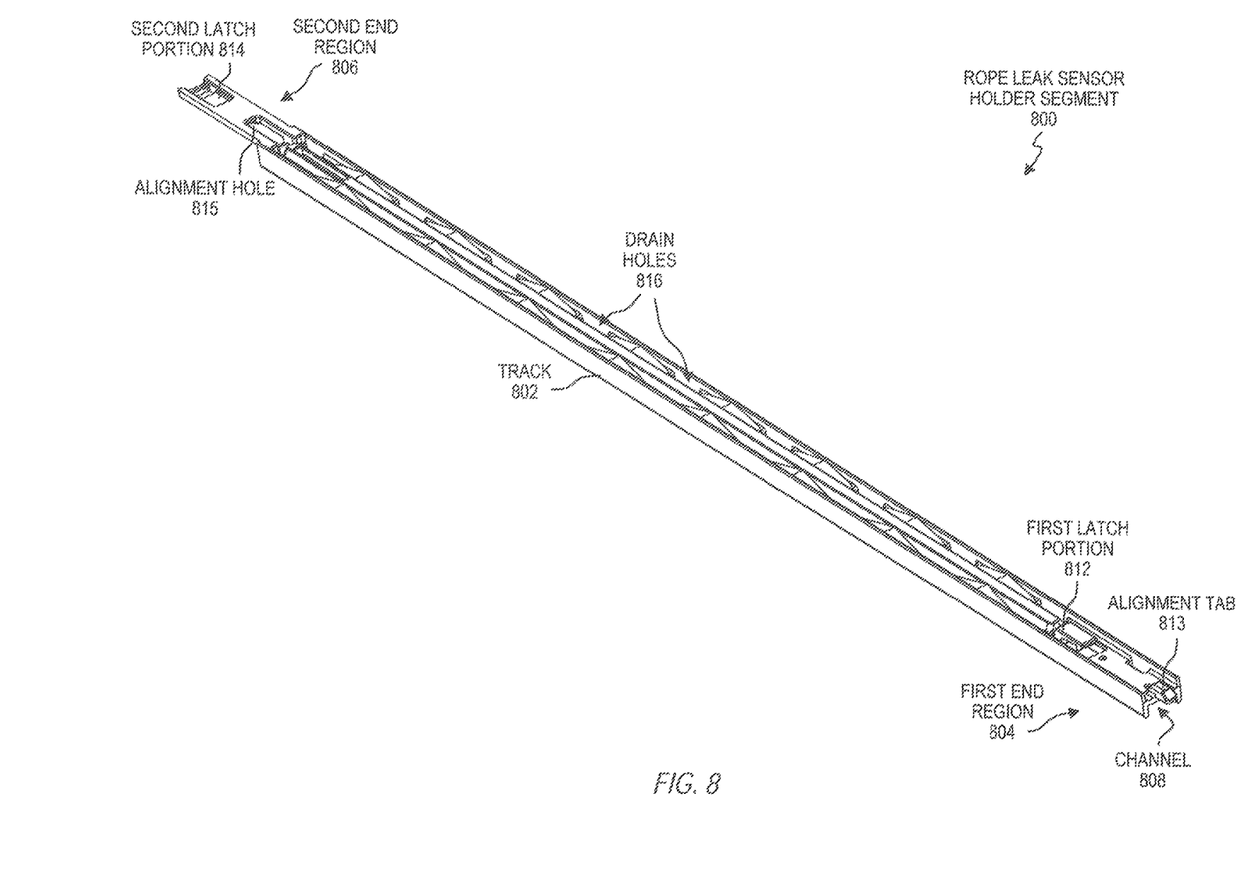
FIG. 8 depicts an example rope leak sensor holder segment.

FIG. 8 depicts an example rope leak sensor holder segment 800. The view shown in FIG. 8 is a perspective view of the holder segment 800 that shows a surface not shown for the holder segment 700 depicted in FIG. 7. That is, where FIG. 7 shows a bottom surface of a holder segment 700, FIG. 8 shows a top surface of a holder segment 800. The holder segment 700 may be an example implementation of the holder segments 100, 200, 502, or 602.

The holder segment 800 includes a track 802 with a channel 808 running lengthwise from a first end region 804 of the track 802 to a second end region 806 of the track 802. The holder segment 800 includes drain holes 816, which allow fluid to flow into the channel 808. In some implementations, the drain holes 816 are analogous to the drain holes 716 of FIG. 7. The track 802 may include sloped portions that funnel fluid into the drain holes 716.

In some implementations, the holder segment 800 includes a first latch portion 812 and an alignment tab 813 at the first end region 804 and includes a second latch portion 814 and an alignment hole 815 at the second end region 806. The first latch portion 812 and the alignment tab 813 may together serve as or form part of the first connector 112, 604, or 712, while the second latch portion 814 and the alignment hole 815 together may serve as or form part of the second connector 114, 606, or 714. The first latch portion 812 may be a hook, and the second latch portion 814 may be a catch complementary to the hook. In operation, a plurality of holder segments 800 may be joined by aligning the alignment tab (e.g., 813) of a first holder segment in the alignment hole (e.g., 815) of a second holder segment, and engaging the first latch portion (e.g., 812) of the first holder segment with the second latch portion (e.g., 814) of the second holder segment.

Figure 9A:
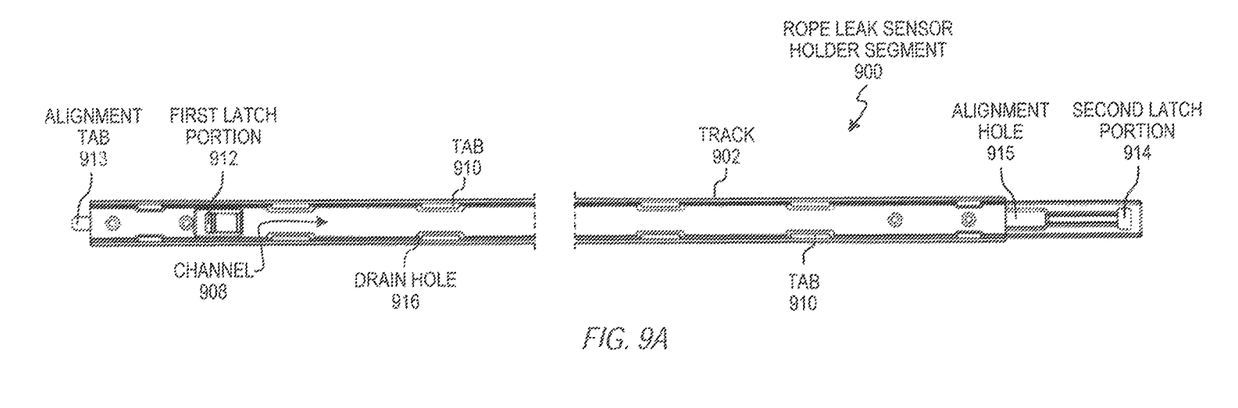
FIG. 9A depicts a bottom view of a rope leak sensor holder segment.

FIG. 9A depicts a bottom view of a rope leak sensor holder segment 900. The holder segment 900 may be analogous in many respects to the holder segments 700 or 800. For example, the holder segment 900 may include a track 902 with a channel 908. The length of the track 902 may be longer or shorter than depicted, as indicated by the break between dashed lines. A rope leak sensor may be assembled into the channel 908 and may be retained by a plurality of tabs 910. In some implementations, the holder segment 900 may include a plurality of drain holes 916 to allow fluid to flow into the channel 908, which may be aligned with the tabs 910 as depicted in FIG. 9A, although other configurations may be employed.

The holder segment 900 also may include a first latch portion 912, an alignment tab 913, a second latch portion 914, and an alignment hole 915, which may be analogous in many respects to the first latch portion 812, the alignment tab 813, the second latch portion 814, and the alignment hole 815 described above, respectively.

Figure 9B:
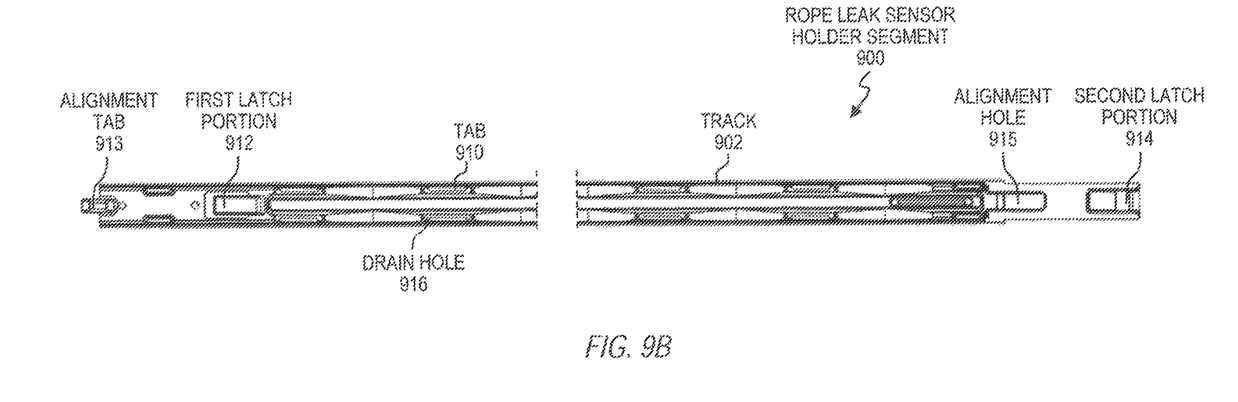
FIG. 9B depicts a top view of a rope leak sensor holder segment.

FIG. 9B depicts a top view of the rope leak sensor holder segment 900 of FIG. 9A. Identical reference numbers in FIG. 9B identify similar or analogous elements described above with respect to FIG. 9A.

Figure 10:
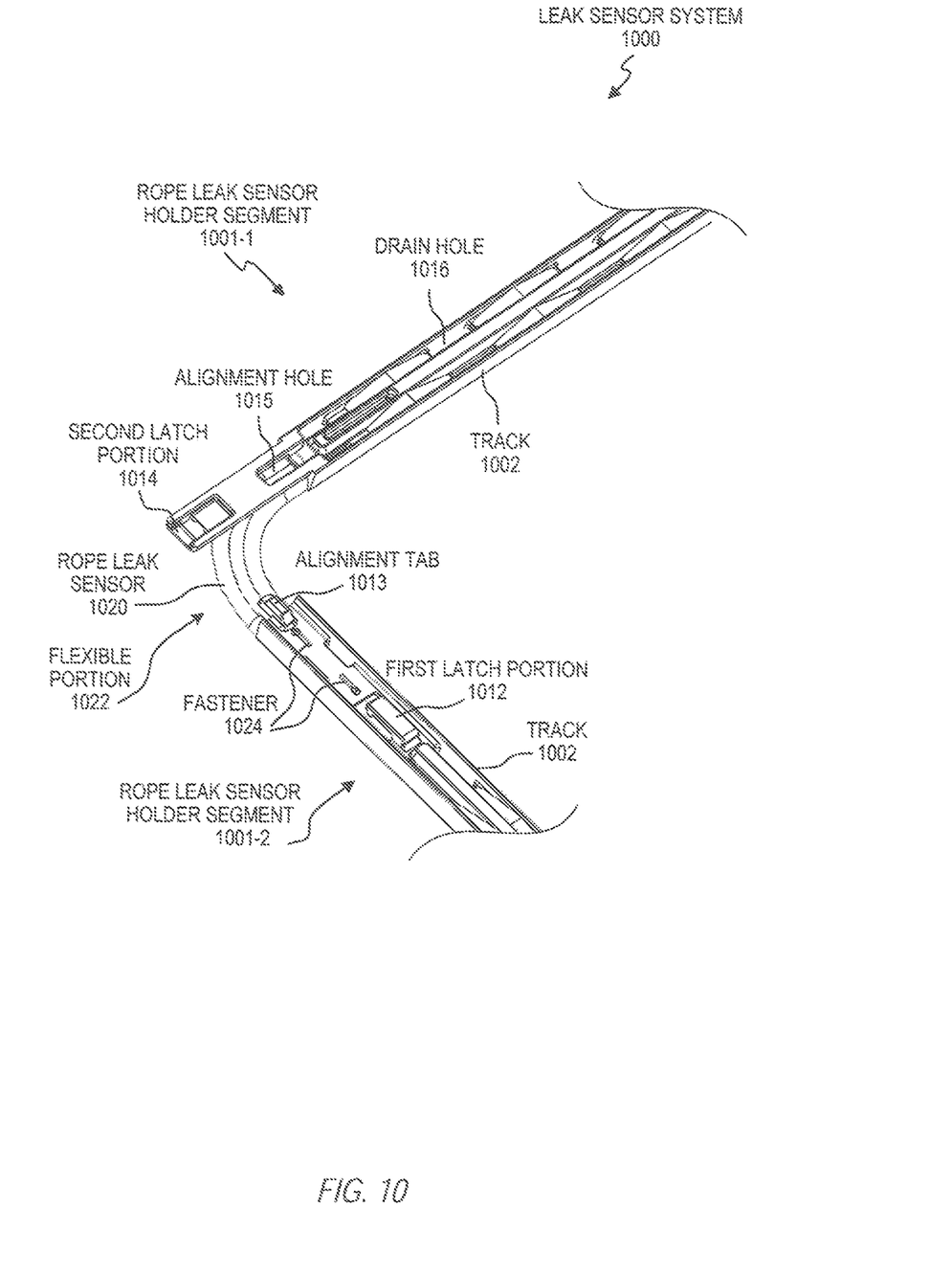
FIG. 10 depicts a leak sensor system with a flexible portion.

FIG. 10 depicts a leak sensor system 1000 with a flexible portion. The leak sensor system 1000 includes a plurality of rope leak sensor holder segments 1001 (and holder segments 1001-1 and 1001-2 in particular). The leak sensor system 1000 also includes a rope leak sensor 1020 assembled into the holder segments 1001. For example, each holder segment 1001 may be analogous in many respects to the holder segments 700, 800, or 900, and may include track 1002 with a channel and retaining tabs. The holder segments 1001 also may include drain holes 1016 through the track 1002, and fluid may flow through the drain holes 1016 into the channel and rope leak sensor 1020 below. The holder segments 1001 also may include a first latch portion 1012, an alignment tab 1013, a second latch portion 1014, and an alignment hole 1015.

In some implementations, the leak sensor system 1000 may include a flexible portion 1022, which is a portion of the rope leak sensor 1020 between adjacent and unconnected rope leak sensor holder segments. For example, as depicted in FIG. 10, the rope leak sensor 1020 is bent into a corner at a flexible portion 1022 between adjacent but unconnected holder segments 1001-1 and 1001-2.

The leak sensor system 1000 also depicts an example implementation of a mechanical fastener, namely a staple 1024 (although other fasteners may be employed alternatively or additionally), employed to affix the rope leak sensor 1020 to the holder segment 1001. The staple 1024 may be employed particularly at the ends of the track 1002 (e.g., analogous to the first end region 104 and/or second end region 102) to prevent the rope leak sensor 1020 from falling out of the channel of the track 1002 near the flexible portion 1022.

Figure 11:
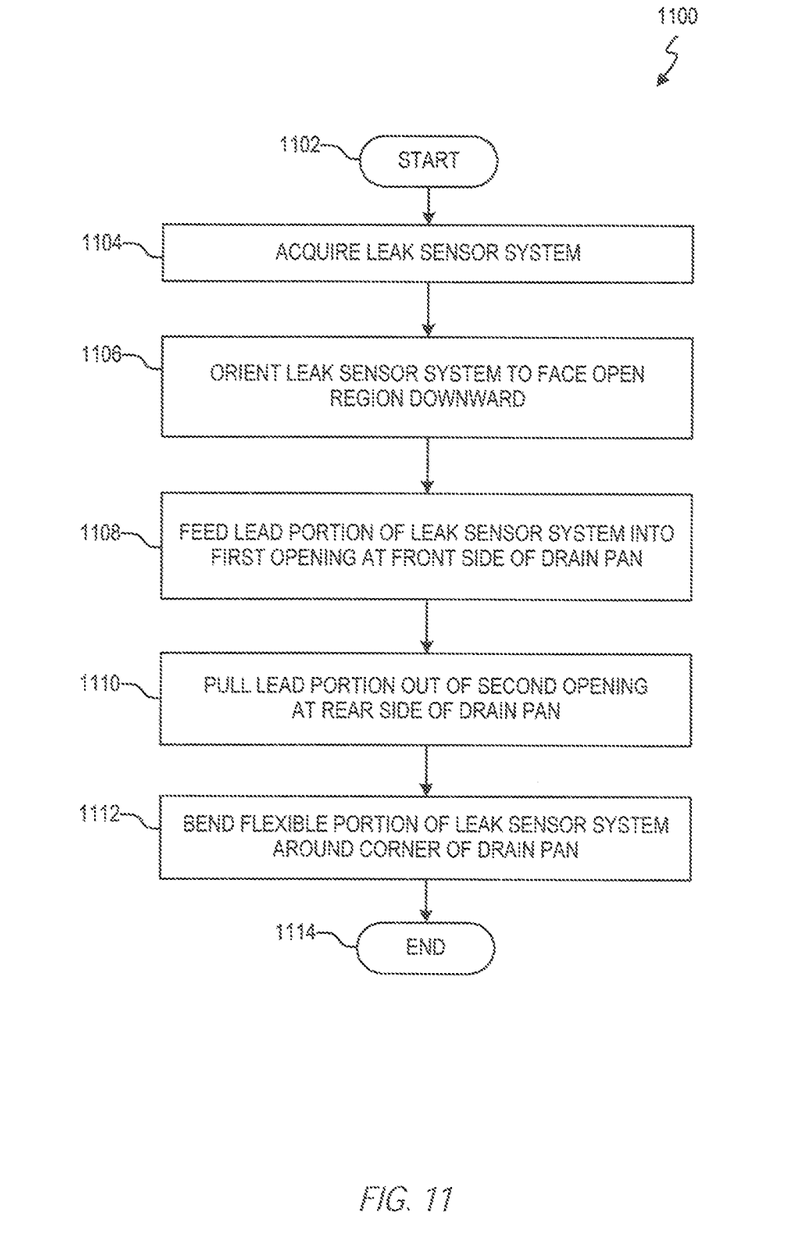
FIG. 11 is a flow diagram depicting an example method for installing a leak sensor system.

FIG. 11 is a flow diagram depicting an example method 1100 for installing a leak sensor system. For example, method 1100 may be useful for installing the leak sensor system 600 into a drain pan for a liquid-cooled computing system.

In some cases, the drain pan is rectangular with a raised support plate occupying a majority of the interior area of the drain pan, thus leaving the outside edge of the drain pan to collect fluid. In particular, a liquid-cooled computing system may be set upon the raised support, and fluid leaked from the computing system may be caught in the drain pan. In some implementations, access to some sides of a rectangular drain pan are open from above, while other sides are at least partially enclosed or obscured (e.g., by a computing system above the drain pan) and accessed via holes or ports at corners of the drain pan. For example, portions of the drain pan may be partially obscured by the computing system.

The method starts at block 1102, and continues to block 1104 where a leak sensor system is acquired. The leak sensor system may include a rope leak sensor assembled to a plurality of rope leak sensor holder segments, where each rope leak sensor holder segment includes a channel extending lengthwise in an elongated track to house the rope leak sensor and retaining tabs along the track extending at least partially across an open region of the channel to secure the rope leak sensor within the channel. For example, the leak sensor system 600 described above may be acquired at block 1104.

At block 1106, the leak sensor system is oriented to face the open region of the channel downward. For example, the leak sensor system so oriented at block 1106 may resemble the holder segment 200 with rope leak sensor 206 installed, as depicted in FIG. 2.

At block 1108, a lead portion of the leak sensor system may be fed into a first opening at a front side of the drain pan. For example, with respect to FIG. 6, the lead portion of the leak sensor system 600 may be an end where the impedance 652 is located. The first opening may be an access into an obscured or enclosed portion of the drain pan. By virtue of the holder segments providing rigid structure around the rope leak sensor, the rope leak sensor may be pushed through the opening and through the drain pan.

At block 1110, the leak sensor system may be pulled out of a second opening at a rear side of the drain pan. In some cases, the leak sensor system may be pulled out through the second opening until a tail end of the leak sensor system is at the first opening. For example, with respect to FIG. 6, a tail end of the leak sensor system 600 may be a portion rope leak sensor 620 that connects to the leak monitor 650.

At block 1112, the leak sensor system may be bent at a flexible portion around a corner of the drain pan. In some implementations, the flexible portion may be a region of the rope leak sensor between adjacent and unconnected rope leak sensor holder segments, such as, for example, flexible portion 622 of FIG. 6. At block 1114, method 1100 may end.

The leak sensor system may continue to be laid in an open edge of the drain pan, fed through access holes, and bent around corners of the drain pan, until the leak sensor system is arranged as desired in the drain pan. For example, the leak sensor system may ultimately be arranged as a rectangular frame inside the perimeter of the drain pan.

In some cases, the drain pan and the computing system sitting in the drain pan may be large (21" by 42", for example). Also, the drain pan and the computing system may be located in a data center or server room. Thus, in some cases, two operators may be involved in installing the leak sensor system. For example, one operator may be at a front side of the drain pan and may perform block 1108 to feed the leak sensor system towards the rear of the drain pan. A second operator may be at a rear side of the drain pan to pull the leak sensor system, fed by the first operator, out the rear of the drain pan (block 1110). The second operator may then bend the leak sensor system around rear corners of the drain pan (block 1112) and feed the leak sensor system back towards the front of the drain pan. The first operator may then receive the leak sensor system fed back towards the front by the second operator. In some implementations, removal of the leak sensor system from the drain pan may be accomplished by performing method 1100 in reverse.

Figure 12:
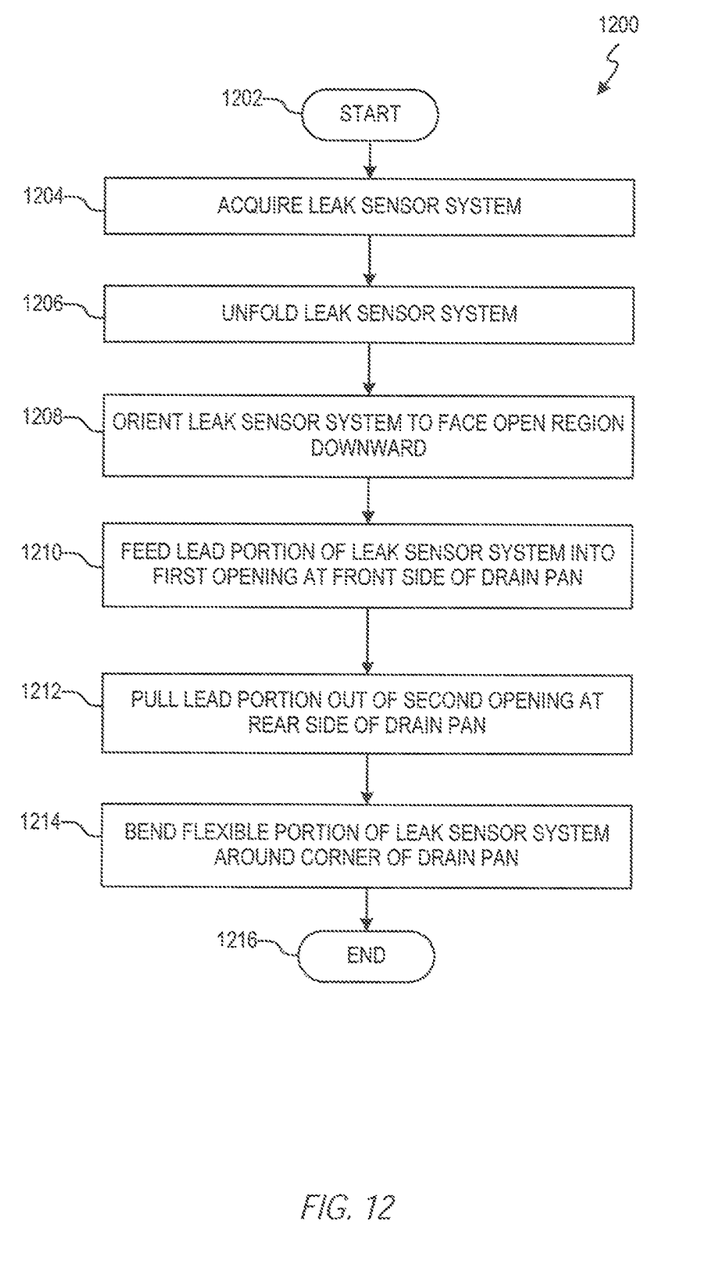
FIG. 12 is a flow diagram depicting another example method for installing a leak sensor system.

FIG. 12 is a flow diagram depicting another example method 1200 for installing a leak sensor system. As with method 1100, method 1200 may be useful for installing a leak sensor system, such as leak sensor system 600, into a drain pan for a liquid-cooled computing system.

The method 1200 starts at block 1202 and proceeds to block 1204, where a leak sensor system is acquired. At block 1206, the leak sensor system is unfolded. For example, the leak sensor system as acquired at block 1204 may be packaged into a compact unit for shipping or for keeping as inventory, by folding the otherwise long leak sensor system (e.g., eighty inches or more) at flexible portions. For example, the leak sensor system 600 depicted in FIG. 6 may be folded at each of the flexible portions 622 to reduce the overall length the system 600.

Blocks 1208, 1210, 1212, 1214 may be analogous in many respects to blocks 1106, 1108, 1110, 1112, respectively. The method 1200 ends at block 1216.

In view of the foregoing description, it can be appreciated that a plurality of rope leak sensor holder segments are provided to facilitate installation or removal of a rope leak sensor from a drain pan of a liquid-cooled computing system and to keep a rope leak sensor flat and straight in a drain pan for consistent and early detection of fluid. Moreover, owing to flexible portions between holder segments, a leak sensor system comprising a rope leak sensor assembled to holder segments may be folded compactly for packaging or storage. A leak sensor system as described may be useful as a field replaceable unit.

In the foregoing description, numerous details are set forth to provide an understanding of the subject matter disclosed herein. However, implementation may be practiced without some or all of these details. Other implementations may include modifications and variations from the details discussed above. It is intended that the following claims cover such modifications and variations.

What is claimed:

1. A rope leak sensor holder segment comprising:
   an elongated track having a first end region and a second end region;
   a channel in the track extending from the first end region to the second end region, the channel to accept a rope leak sensor;
   a retainer to secure the rope leak sensor within the channel;
   a first connector at the first end region; and
   a second connector at the second end region, complementary to the first connector.

2. The rope leak sensor holder of claim 1, wherein the first connector includes an alignment tab and a first latch portion, and the second connector includes an alignment hole and a second latch portion complementary to the first latch portion.

3. The rope leak sensor holder of claim 1, wherein the retainer includes a cap that removably fits into the channel.

4. The rope leak sensor holder of claim 1, wherein the retainer includes a fastener to hold a material of the rope leak sensor.

5. The rope leak sensor of claim 1, wherein the retainer includes a plurality of tabs protruding from the track and at least partially over an open region of the channel.

6. The rope leak sensor holder of claim 1, further comprising a drain hole through the track, extending from an outer surface of the track to the channel.

7. The rope leak sensor holder of claim 1, wherein the channel is in an underside of the track and an open region of the channel faces downward.

8. A leak sensor system comprising:
   a plurality of rope leak sensor holder segments, each rope leak sensor holder segment of the plurality including:
      an elongated track,
      a channel running lengthwise in the track, and
      retaining tabs along the track that extend at least partially across an open region of the channel,
   a rope leak sensor assembled into the channel of each rope leak sensor holder segment and retained by the retaining tabs.

9. The leak sensor system of claim 8, wherein the plurality of rope leak sensor holder segments are oriented to face each open region downward.

10. The leak sensor system of claim 9, wherein the rope leak sensor holder segments include drain holes that extend through the track from an upper surface of the track into the channel.

11. The leak sensor system of claim 8, wherein each rope leak sensor holder segment includes a first connector at a first end region of the track and a second connector at a second end region of the track, and
   rope leak sensor holder segments are joined by mating the first connector and second connector of respective adjacent rope leak sensor holder segments.

12. The leak sensor system of claim 11, wherein at least some adjacent rope leak sensor holder segments are joined, and
   a portion of the rope leak sensor between adjacent and unconnected rope leak sensor holder segments is a flexible portion.

13. The leak sensor system of claim 12, further comprising a corner finishing element to set an angle of the flexible portion.

14. A method comprising:
   acquiring a leak sensor system that includes a rope leak sensor assembled to a plurality of rope leak sensor holder segments, each rope leak sensor holder segment of the plurality including:
      a channel extending lengthwise in an elongated track to house the rope leak sensor, and
      retaining tabs along the track extending at least partially across an open region of the channel to secure the rope leak sensor within the channel;
   orienting the leak sensor system to face the open region downward;
   feeding a lead portion of the leak sensor system into a first opening at a front side of a drain pan;
   pulling the lead portion out of a second opening at a rear side of the drain pan; and
   bending, after the pulling, a flexible portion of the leak sensor system around a corner of the drain pan, the flexible portion being a region of the rope leak sensor between adjacent and unconnected rope leak sensor holder segments.

15. The method of claim 14, further comprising unfolding the leak sensor system after the acquiring, wherein the leak sensor system as acquired is folded at the flexible portions.

* * * * *